United States Patent [19]
Karas et al.

[11] 3,984,205
[45] Oct. 5, 1976

[54] FLAME IONIZATION DETECTOR

[75] Inventors: Edwin L. Karas, Sharon; Paul J. Lincourt, Franklin; John P. Callahan, Hanson; Earl E. Whitamore, Foxboro, all of Mass.

[73] Assignee: The Foxboro Company, Foxboro, Mass.

[22] Filed: Sept. 10, 1975

[21] Appl. No.: 611,948

[52] U.S. Cl. ............................................. 23/254 EF
[51] Int. Cl.² ........................................ G01N 31/12
[58] Field of Search ................... 23/254 EF; 73/23.1

[56] References Cited
UNITED STATES PATENTS

| | | | |
|---|---|---|---|
| 2,991,158 | 7/1961 | Harley | 23/254 EF |
| 3,086,848 | 4/1963 | Reinecke | 23/254 EF |
| 3,340,013 | 9/1967 | Rooney et al. | 23/254 EF |
| 3,372,000 | 3/1968 | Gallaway et al. | 23/254 EF |

*Primary Examiner*—Robert M. Reese
*Attorney, Agent, or Firm*—Frank J. Fleming

[57] ABSTRACT

A flame ionization detector adapted for use in hazardous areas and for mounting in any attitude, capable of using as small a flame as can be dependably maintained because of an arrangement of the flame at the open end of a thin-walled small diameter tubular electrode inside a relatively long open ended cylindrical collector and the regulation of the rates of flows which make it possible to maximize the sensitivity of the detector to the presence of an organic vapor. Excess air is maintained at a predetermined minimum. The inside diameter of the collector is made approximately twice the visible diameter of the widest point of the flame. A curtain of air flowing at a predetermined rate through the annular passage between the electrode and collector is directed into encompassing contact with the flame and the proximity of the collector to the flame maintains a relatively dense ion bearing layer of gases at the surface of the collector. A catalytic ignitor is provided with an externally operated manual switch for cleaning the ignitor.

10 Claims, 4 Drawing Figures

FLAME IONIZATION DETECTOR

FIELD OF THE INVENTION

This invention relates to flame ionization detectors for industrial use in quantitatively sensing the presence of an organic vapor in a fluid stream. It is more particularly related to the type of flame ionization detector having a cylindrical collector electrode and the flame at the open end of a tubular electrode.

FIELD OF THE PRIOR ART

This invention is in a crowded field of art. The following is a list of articles and United States Patents representative of the art in this field:

A. "Ionization Detectors in Gas Chromatography" by J. Kruger, a Thesis, Technological University Eindhoven, June 1964.
B. "Ion Current Measurement of Gas Chromatographic Effluents with a Selective Hydrogen Flame Ionization Detector" by McCoy and Cram, Journal of Chromatographic Science, Volume 7, January 1969, Pages 17–23.
C. "Quantitative Gas Chromatographic Analysis of Hydrocarbon with Capillary Columns and Flame Ionization Detector" by Bruderreck, Schneider and Halasz, Analytical Chemistry, Volume 36, No. 3, March 1964, Pages 461–473.
D. "A Hydrogen Flame Ionization Detector for Martian/Lunar Life Detection Experiments" by Lucero, Smith and Johnson, ISA Transactions, Volume 10, No. 1, Pages 58–66, 1971.
E. "A Study of the Flame Ionization Detector" by McWilliams, Journal of Chromatography, 51 (1970) Pages 391–406.
F. "A Flame Ionization Detector for Work Under Controlled Pressures," by Bocek, Novak and Janak, Journal of Chromatographic Science, Volume 8, April 1970, Pages 226–228.
G. "High Performance Flame Ionization Detector System for Gas Chromatography" by Smith, copyrighted by Hewlett-Packard Company 1973.
H. "The Flame Ionization Detector, A Theoretical Approach" by Dewar, Journal of Chromatography, 10 (1961) Pages 312–323.

U.S. Pat. Nos.
Harley: 2,991,158
McWilliams: 3,039,856
Reinecki: 3,086,848
Krzeminski et al.: 3,175,886
Rooney et al.: 3,340,013
Gallaway et al.: 3,372,000
Brittan et al. 3,473,895

In his patent, McWilliams defines the operation of a flame ionization detector as a method of detecting the presence of an organic vapor in a gas which comprises passing the gas into the region of the combustion zone of a hydrogen fuel flame and detecting the change in the electrical conductivity of the flame consequent upon the presence of the organic vapor. He shows the detector diagramatically with the burner tube serving as one electrode and a wire gauze over the flame serving as the collector electrode. All of the articles and other patents cited above disclose enclosed detectors having a variety of arrangements of passages and electrodes.

Inasmuch as the present invention is an improved arrangement of passages and electrodes for increasing the sensitivity of the detector to the presence of organic vapors, the following quotation from the first paragraphs of Articles F and B respectively point out the difficulty of the problem solved by this invention:

"The flame ionization detector is characterized by remarkable variability of its properties. Previous studies have indicated that there is scarcely any operating parameters, which when changed, does not bring about substantial changes in the performance of the detector."

"A large number of papers describing the optimization of the experimental parameters and the design of the detector have been reported although generally from a trial and error approach rather than from investigations of specific flame ionization reactions."

Examination of each of the references cited above in the light of this invention as described later herein will confirm that none of the flame ionization detectors disclosed use the combination of the invention.

SUMMARY OF THE INVENTION

In a flame ionization detector, several of the critical parameters of the ionization process become fixed by the dimension and arrangement of the parts in the vicinity of the flame. Other parameters may be varied by varying the rates of flow and ratios of hydrogen, and organic vapor. Each of the fixed and variable parameters will be discussed in order to provide a better appreciation of the merits of this invention.

Flame temperature affects the ionization process and the ultimate sensitivity of a detector. Therefore, it is important to maintain the flame at a temperature which results in maximum sensitivity. In order to do this, sufficient air must be supplied to the flame to insure complete combustion. Although excess air must be furnished to insure complete combustion, an excessive amount of excess air will result in cooling the flame. Turbulent air at the exterior of the flame also will result in cooling the flame. Therefore, it is important to provide some excess air but not such an amount that it will cool the flame and the air must be brought into contact with the flame in a manner which causes the least turbulence.

Flame temperature will be reduced by conducting heat away from the flame when the collector is located too close to the flame. Therefore, it is important to make the inside diameter of the collector large enough to prevent it from lowering the temperature of the flame.

In addition to reducing the flame temperature, overheating the collector will cause thermionic emissions which will appear as noise in the output signal from the detector. In the burning process, carbon particles may be formed. If a glowing carbon particle drops onto the edge of the burner tube, it causes thermionic emission. Therefore, it is important to prevent thermionic emissions from either the collector or impurities which are detrimental to the output signal.

It is believed that the site of ion formation from organic molecules is a thin layer at the base of the flame and that the upper part of the flame contributes nothing to ion formation. After formation, the ions are believed to fan out progressively as they move further from the base. In the process of fanning out, the ion laden gas will be diluted by the air encompassing the flame. The sensitivity of the detector is decreased as a result of the reduction in density of the ion laden gas adjacent to the surface of the collector. Therefore, it is important to locate the surface of the collector sufficiently near the flame so as to be in the region in which the ion laden gas is densest.

For economical reasons, it is desirable to use as low a rate of flow of hydrogen and organic vapor as possible. In prior art detectors, when the rate of flow of hydrogen and organic vapors was reduced, the sensitivity became correspondingly less. Therefore, it is important that the smallest flame that can be used or can be dependably maintained is used providing the detector can be made correspondingly more sensitive.

In order to use a flame ionization detector in a hazardous location it must conform to safety codes. Inasmuch as a detector operates with flammable gas, the body of the detector must be constructed strong enough to withstand an internal explosion. When the detector is used in a hazardous area the outside of the detector must remain below a prescribed safe temperature and if an explosion occurs inside, the flame resulting from the explosion must be confined so as not to ignite the external atmosphere. The force of an explosion is proportionally greater with an increase in the volume of the gas ignited. Therefore, it is important to not only make the body of the detector strong, but to make its internal volume as small as possible. The flame of an explosion is contained by using long, small diameter passages through which a flame front can not pass. Therefore, in order to meet the safety code for these passages, the flow of gasses therethrough must be small.

When the products of combustion are in a gaseous phase, they will flow out of the detector without depositing any corrosive acids on the surfaces of the vent passage. If the temperature of products of combustion falls below the dew point of the mixture, then the water and combustion products mix to produce an acid. Any corrosion products deposited on the vent passage will form a resistance to flow. In view of the requirement for a long small diameter vent passage to meet safety codes, any deposit will seriously affect the operation of the detector. Therefore, it is important that the materials used in the body and vent passage of the detector be strong enough to contain any explosion, be capable of maintaining an internal temperature above the dew point of the products of combustion and an outside temperature below that which would cause an external explosion, and be corrosion-proof.

The electrical measuring circuit of a flame ionization detector must impose a high enough voltage across the flame to collect ions in the flame and sensitive enough to the conductivity of the ion stream to sense its amplitude. Any capacitive coupling to conductive points in the body of the detector can be detrimental to the measurement. Therefore, it is important to use a material for the body of the detector which is not conductive so as to avoid capacitive coupling problems.

For application to a continuous industrial process, it is essential that the flame in the detector be easily ignited from an externally operated ignitor. In the event of a flame-out, the ignitor must be capable of reigniting the flame. In order to insure that the ignitor will operate reliably, it is desirable that means are available to clean the ignitor periodically.

It is therefore the primary object of this invention to provide an improved flame ionization detector in which parameters relating to the ionization formation are fixed by an arrangement of the tubular electrode and cylindrical collector in the vicinity of the flame in a manner which maximizes the sensitivity of the detector to the presence of an organic vapor.

It is an object of this invention to provide an improved flame ionization detector with maximized sensitivity which is economical to operate.

It is another object of this invention to provide an improved flame ionization detector which meets safety codes for use in hazardous areas.

It is still another object of this invention to provide an improved flame ionization detector which is not affected by corrosive hydrocarbons.

It is a further object of this invention to provide an improved flame ionization detector which can be mounted in any attitude without affecting its operation.

A still further object of this invention is to provide an improved flame ionization detector having an ignitor which automatically acts to reignite the flame in the event of a flame-out.

Yet another object of this invention is to provide an improved flame ionization detector with an ignitor which may be cleaned by manually operable external means.

The above objects are achieved, in part, by inserting the flame bearing end of a thin-walled small diameter tubular electrode a preselected distance into one end of a relatively long open-ended cylindrical collector and regulating the rates of flow and the proportions of air and hydrogen bearing organic vapor to the flame. Inasmuch as the dimensions and flow rates have an interacting affect on the parameters of ignition formation, the combination of this invention is a compromise which has been found to provide the maximum sensitivity of the detector.

The size and temperature of the flame is basically established by regulating the ratio and flow of hydrogen and air to the flame.

The inside diameter of the collector is made twice the visible diameter of the flame at its widest point. This ratio of diameters positions the inner surface sufficiently far from the flame so it will not cool the flame or heat the collector sufficiently to cause thermionic emissions. In addition, the surface is sufficiently close to be in the region of the dense ion laden gas. This later affect will be discussed more fully later herein.

The outer surface of the tubular electrode and the inner surface of the cylindrical collector form an annular passage. The rate of flow of air through the annular passage is regulated. How this flow is regulated will be described later herein. The rate of flow is of a sufficiently greater magnitude than the convection currents created by the heat of the flame so the detector may be mounted in any attitude without affecting its operation. This feature makes it possible to mount the detector in an inverted position so that any particles of carbon formed will drop out of the region of the flame. Thus, the flame is self-cleaning and the particles cannot lodge in the proximity of the flame where they might be heated sufficiently to cause thermionic emissions.

The curtain of air issuing from the annular passage encompasses the exterior of the flame. The length of the annular passage is sufficient to reduce turbulence to a minimum. The tubular electrode is made thin-walled and with a uniform diameter so that the inner wall of the air curtain will contact the flame at a point as near as possible to the site of ionization formation. A thick walled tube with either a square end or a tapered tip causes a pressure drop as the flowing air passes the tip which adversely creates turbulence and the availability of the air in the proximity of the site of ion formation.

The fanning out of the ion laden gas is limited by the proximity of the inner surface of the collector to the flame. The spacing is such that the ion bearing layer adjacent to the surface of the collector is relatively dense and the upward sweep by the curtain of air insures that the relatively dense ion bearing gas passes in contact with a large area of the surface of the collector. In the process of maintaining the ion laden gas dense adjacent to the surface of the collector, this spacing also insures the maximum contact of the air with the flame which results in complete combustion of the hydrogen. A predetermined minimum amount of excess air is supplied to reduce the cooling affect thereof to a minimum.

In operation, the pressure of hydrogen from a high pressure source is reduced to a predetermined amplitude by a pressure regulator and in the example shown, the organic vapor to be sensed by the detector is added to the hydrogen as the hydrogen flows through a chromatographic column. The pressure of the mixture is further reduced as it flows through a capillary restrictor. The pressure of air from a high pressure zero air source is reduced to a predetermined value by a pressure regulator and further reduced as it flows through a capillary restrictor. At this point the air stream is divided so that one branch stream flows through a small orifice and passage into a chamber in the detector. This branch stream then flows through the annular passage to supply air to the exterior of the flame. The second branch stream of air flows through a small orifice to blend with the stream of hydrogen and organic vapor and thence through the tubular electrode to be consumed by the flame. The ratio of air to hydrogen is maintained by the settings of the regulators and the capillary restriction in each stream. The proportions of the air added to the hydrogen-organic vapor stream and that flowing into the detector for contact with the exterior of the flame is determined by the sizes of the two small orifices. Inasmuch as the rate of flow of air into the detector is regulated, the rate of flow of air through the annular passage is dependent upon the differential pressure across the ends of the collector.

Inasmuch as it is desirable to use as little hydrogen as possible, the detector is proportioned to the smallest flame that can be dependably maintained. This reduces the internal capacity to considerably under that required to meet safety code specifications for an explosion-proof structure. Similarly the passages are reduced in diameter and of sufficient length to meet the code requirements for flame-proof passages.

In order to avoid corrosive affects, the interior of the detector is made sufficiently small and heat is dissipated in the interior so that the products of combustion are maintained at a temperature above their dew point. In order that corrosion will be eliminated, all parts of the detector that are in contact with the products of combustion are made of a non-corrosive material such as alumina. The non-corrosive material selected is also non-conductive so as to eliminate any detrimental capacitive coupling.

The detector is assembled by cementing the cover to the body. An ignitor is sealed in the exhaust chamber. This ignitor is a heated catalyst which, when in a flammable mixture of hydrogen and air will ignite the mixture. By using this type of ignitor, the flame will automatically be relighted in the event of a flame out. In time, the igniter coil may become too contaminated to operate. With the cemented construction it is difficult to clean a contaminated ignitor from the inside of the detector. In order to overcome this difficulty a manually operated switch is provided which supplies current to heat the ignitor coil sufficiently to burn off the contaminants.

DESCRIPTION OF THE DRAWINGS

The objects and advantages of this invention will be more fully understood from the description taken in connection with the accompanying drawings, wherein.

DESCRIPTION OF THE PREFERRED EMBODIMENTS

Figure 1:
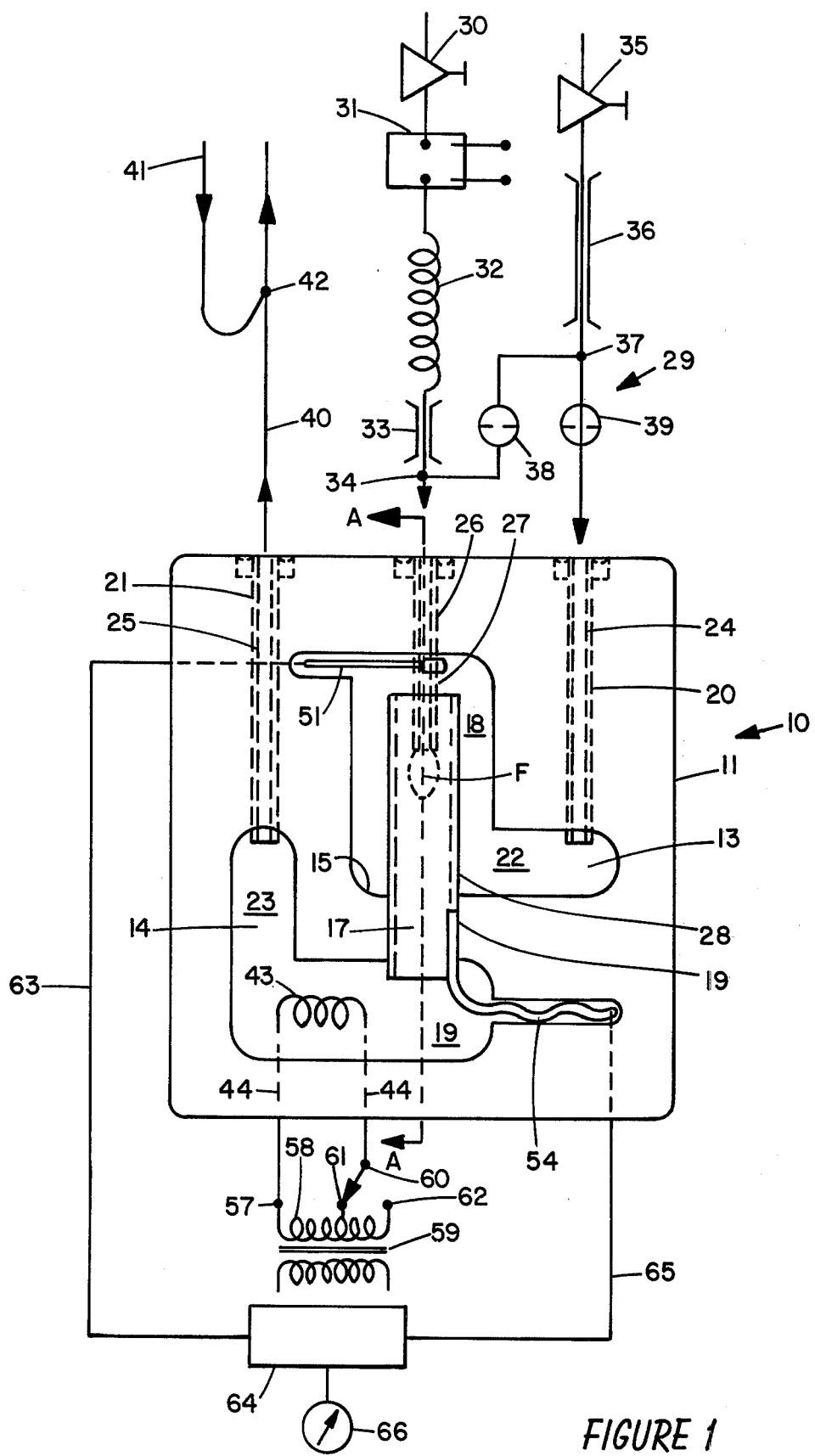
FIG. 1 is a plan view of the flame ionization detector of this invention with the cover removed to show the interior thereof, and includes diagramatic representations of the streams to and from the detector and of the electrical circuits connected to the detector.
Figure 2:
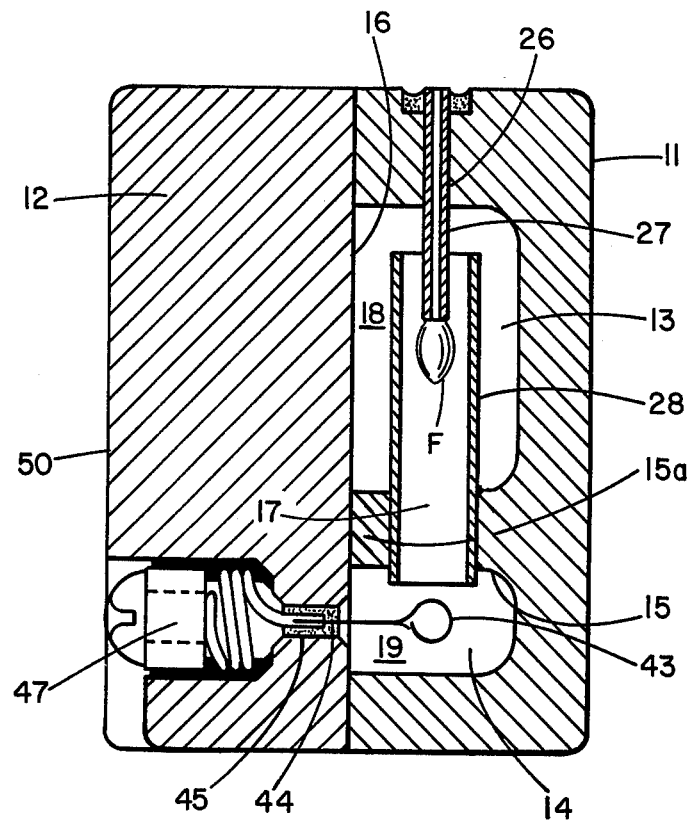
FIG. 2 is a cross-sectional view of the body and cover taken along the line A—A in FIG. 1.

Referring to FIGS. 1 and 2, the flame ionization detector 10 has a body 11 and cover 12 preferably made of a non-conductive material such as a ceramic which will not corrode in the presence of the products of combustion. The material selected must be strong enough to withstand an explosion and must dissipate heat so the outside temperature will not exceed that prescribed by safety codes. Alumina has been found to be a satsifactory material which meets these requirements.

The body 11 has an L-shaped air chamber 13, an L-shaped exhaust chamber 14 separated by a common wall 15. A portion of common wall 15 is the insert 15a shown in FIG. 2 which is used so that the surface 16 of cover 12 may be made flat. A passage 17 in wall 15 provides communication between the leg 18 of air chamber 13 and leg 19 of exhaust chamber 14. Passages 20 and 21 extend through the body 11 to provide communication from the exterior of body 11 to legs 22 and 23 of air chamber 13 and exhaust chamber 14 respectively. Ceramic tubes 24 and 25 are inserted and cemented in passages 20 and 21 respectively to provide the precise diameter and length required to meet safety codes for flame-proof construction. Passage 26 extends through the wall of body 11. Burner tube 27 is inserted through passage 26 and extends a predetermined distance into leg 18 of chamber 13 in axial alignment with passage 17. The burner tube 27 is made of a metal, such as stainless steel. A relatively long cylindrically shaped collector 28 is inserted and cemented in passage 17 so that one end extends into leg 18 of air chamber 13 to overlap axially burner tube 27 a predetermined distance. Collector 28 extends a short distance into leg 19 of exhaust chamber 14. Cover 12 is cemented to body 11 to complete chambers 13 and 14, with the electrical connection in place as will be described hereinbelow.

Now referring to the diagram 29, shown above the detector 10, hydrogen is fed from a pressurized supply through regulator 30. Regulator 30 is adjusted to a predetermined value. The hydrogen flows at a controlled pressure through sample switch 31 to chromatographic column 32. A sample of the hydrocarbon to be separated by column 32 is introduced into the flowing stream by sample switch 31. The operation of chromatographic column 32 is well known so needs no explanation. The hydrogen-organic vapor mixture leaving column 32 flows through capillary restrictor 33 which reduces its pressure. From the capillary restrictor 33, the mixture flows to junction 34. At junction 34 air is blended with the hydrogen-organic vapor mixture. The hydrogen-organic vapor-air mixture flows through burner tube 27 to the flame.

Air from a pressurized zero air source is fed through pressure regulator 35. Regulator 35 is adjusted to a predetermined value. The air flows through capillary restrictor 36 which reduces its pressure. The air flows from capillary restrictor 36 to junction 37 where it is divided into two streams. One stream flows through orifice 38 to junction 34 where it blends with the hydrogen-organic vapor mixture flowing from capillary restrictor 33. The orifice 38 may be, for example, a jewel having an orifice diameter of 0.008 inches with a wire having a diameter of 0.005 inches in the orifice. The other stream flows through orifice 39 and through tube 24 into chamber 13. Orifice may be, for example, a jewel having an orifice diameter of 0.008 inches. The selection of the sizes of the orifices 38 and 39 is to divide the streams so that the mixture being burned will contain 25 percent and the air entering chamber 13 will provide 75 percent of the air required for complete combustion with a small controlled amount of excess air.

Exhaust gases flow out of chamber 14 through vent passage 25 and conduit 40 to atmosphere. Purge air is sometimes supplied through conduit 41 and junction 42. The flame ionization detector 10 is made to plug into a manifold, not shown, for connection to the flow lines shown diagramatically in FIG. 1.

Figure 3:
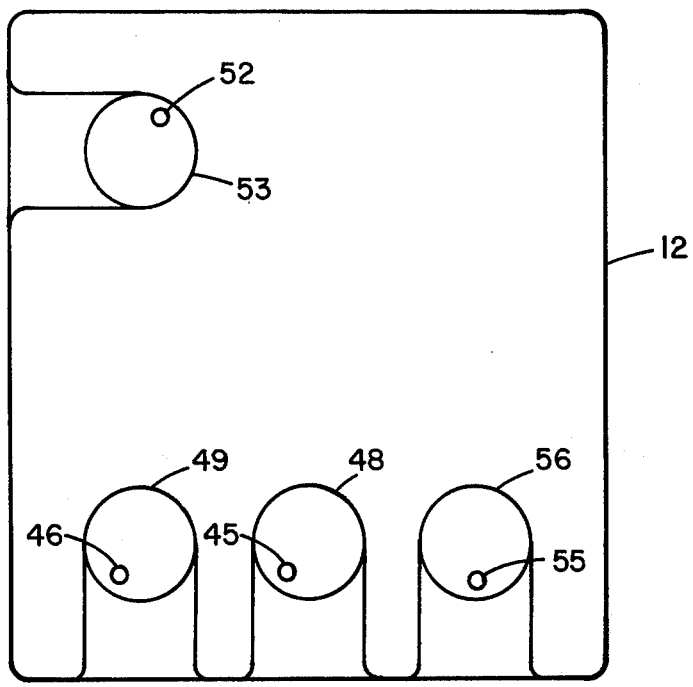
FIG. 3 is a plan view of the cover.

Now referring to FIGS. 1, 2 and 3, an ignitor coil 43 is mounted on cover 12 with lead wires 44 extending through passages 45 and 46. The ignitor coil 43 is located so when the cover is in place on body 11, it extends into chamber 14. Lead wires 44 are attached to connection 47, one of which is shown in FIG. 2. Connectors 47 are mounted in recesses 48 and 49 on the outside surface 50 of cover 12. Lead wire 51 is attached to burner tube 27 and extends through passage 52. Lead wire 51 is attached to a connector 51a, not shown, which is mounted in recess 53 on the outside surface 50 of cover 12. Lead wire 54 is attached to collector 28 and extends through passage 55. Lead wire 54 is attached to a connector, not shown, which is mounted in recess 56 on the outside of surface 50 of cover 12.

Now referring to FIG. 1, terminal 57 of secondary 58 of transformer 59 is connected to one connector 47 on cover 12 which, in turn, is connected to one of the lead wires 44 of ignitor coil 43. Switch 60 is connected to the other connector 47 on cover 12, which in turn, is connected to the other lead wire 44 of ignition coil 43. Switch 60 is shown connected to terminal 61 on secondary 58. Switch 60 may be manually moved into contact with terminal 62 of secondary 58.

Lead wire 63 of measuring apparatus 64 is connected to the connector (not shown) mounted in recess 53 of the cover 12 which, in turn, is connected by lead wire 51 to burner tube 27. Lead wire 65 of measuring apparatus 64 is connected to a connector (not shown) mounted in recess 56 of the cover 12, which, in turn, is connected to lead wire 54. A suitable readout device 66 is provided.

In operation, the hydrogen-organic vapor-air mixture flows through burner tube 27. The hydrogen is ignited by catalytic action as it comes into contact with ignitor coil 43 which is heated by the current flowing in the portion of the secondary 58 between terminals 57 and 61. Measuring apparatus 64 supplies a voltage through the flame from the tip of burner tube 27 to collector 28. In the event the ignitor coil 43 becomes dirty, it may be cleaned by manually moving switch 60 from terminal 61 to terminal 62 to increase the current flow through the ignitor coil 43 for a short period. When clean, the switch is returned to terminal 61. In the event of a flame-out, the hydrogen will be reignited when it comes in contact with the heated catalytic ignitor coil.

The flow of the air into chamber 13 and the flow of the hydrogen-organic vapor mixture are carefully regulated by the settings of regulators 35 and 30 respectively and the ratio of the air blended with the mixture to the air supplied in chamber 13 is regulated by the ratio of orifice 38 and 39. The air inlet tube 24 and burner tube 27 may cause a slight pressure drop and must be included in calculating the flows. Vent tube 25 may also cause a slight restriction to the flow of products of combustion, resulting in a slight back pressure in chambers 13 and 14.

The collector 28 has an inside diameter of approximately twice the visual diameter of the flame. This ratio of diameters was determined by extensive testing to keep the collector far enough from the flame so it caused no cooling of the flame and to keep the temperature of the collector below the level at which thermionic emission occurs. Further, the ratio of diameters located the surface of the collector at a distance from the flame at which the density of the ion laden gases is maintained high.

The length of the annular passage formed by the extension of the burner tube into the open end of the collector is predetermined so that the curtain of air encompassing the flame is not turbulent.

In one embodiment of the flame ionization detector of this invention, the internal volume of body 11 was made 1 cubic centimeter. With this small volume, the alumina body 11 was strong enough to meet the requirements of safety codes for explosion-proof bodies. The air inlet tube 24, burner tube 27 and vent tube 25 provided flame-proof passages which met the code requirements for flame-proof structure without offering deleterious restrictions to flow.

Figure 4:
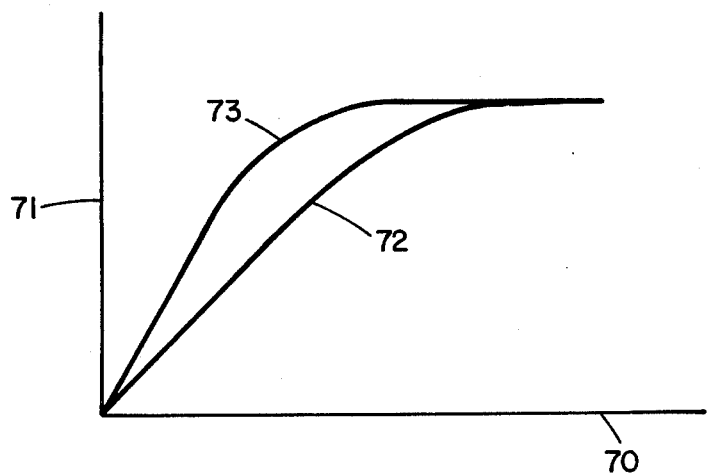
FIG. 4 is a graph comparing the sensitivity of the flame ionization detector of this invention with a prior detector.

Now turning to FIG. 4, the graph shows the relative sensitivity of the flame ionization detector of this invention as compared to the type shown in FIG. II of Rooney, et al. U.S. Pat. No. 3,340,013. Hydrogen-Air flow is plotted on horizontal ordinate 70 and coulombs per gram atoms of carbon is plotted on the vertical ordinate 71. Curve 72 shows the values for the Rooney et al detector and curve 73 those for the detector of this invention. An example of the difference in flow rate in cc/min. and coulombs per gram atom is as follows:

| Rooney et al Detector | |
|---|---|
| Carrier (N2) | 60 |
| Fuel (H2) | 40 |
| Air | 300 |
| Coulombs per gram atom of carbon | 0.17 |

| Detector of this Invention | | |
|---|---|---|
| Fuel (H2) | 40 | 25 |
| Air in Fuel | 40 | 25 |
| Air to Exterior of Flame | 120 | 75 |
| Coulombs per gram atoms of carbon | 0.40 | 0.34 |

The sensitivity, coulombs per gram atoms of carbon for competitive detectors has been found to be generally near 0.25 or less.

The flow velocity of air through collector 28 for the above rates is approximately one foot per second. This rate is sufficiently high with respect to the flow induced by convection to make it practical to mount the detector 10 in any attitude. By mounting the detector with the flame F extending downward, any particles in the flame will drop into chamber 19. Thus, the particles will not lodge on the end of burner tube 27 where, if glowing, they may cause thermionic emissions.

Using a "hypodermic" tube having an 0.016 inch id, the visible diameter of the widest portion of the Flame F is about 0.050 inch – 0.060 inch and the inside diameter of the collector 28 is 0.125 inch. These dimensions are illustrative only of the small size possible with this detector. The general principles taught herein apply to any detector, regardless of its size.

We claim:

1. A flame ionization detector adapted to be connected to measuring apparatus, comprising, in combination:
    a housing having
        an air chamber,
        an exhaust chamber,
        an internal passage providing communication between said air chamber and said exhaust chamber,
        an air inlet passage providing communication from the exterior of said housing to said air chamber,
        a burner tube insert passage providing communication from the exterior of said housing to said air chamber, and
        a vent passage providing communication from said exhaust chamber to the exterior of said housing;
    a burner tube inserted in said burner tube insert passage with one end thereof extending into said air chamber;
    a cylindrical collector insert in said internal passage with one end thereof extending into said air chamber in axial alignment with said burner tube;
    means for supplying a mixture of fuel and organic vapor to be sensed to said burner tube;
    means for supplying air to said detector, said means for supplying said air having divider means adapted to supply a portion of said air to said burner tube and a portion of said air to said air inlet passage at a controlled ratio;
    said means for supplying said mixture to said burner tube and said means for supplying said air to said device each have control means with operable ranges adapted to cooperate during operation of said detector to regulate the size of a flame burning at said one end of said burner tube;
    said cylindrical collector having an inside diameter approximately eight times the inside diameter of said burner tube and disposed so that said one end of said burner tube extends into said one end of said cylindrical collector;
    terminal means for connecting said burner tube and said cylindrical collector to said measuring apparatus.

2. The flame ionization detector in accordance with claim 1 wherein said distance said burner tube extends into said cylindrical collector forms an annulus passage adapted to provide a restriction to the rate of air flow through said annulus passage.

3. The flame ionization detector in accordance with claim 1 wherein said housing includes;
    a body with a cover cemented thereto.

4. The flame ionization detector in accordance with claim 1 further comprises:
    an ignitor means in said exhaust chamber.

5. The flame ionization detector in accordance with claim 4 wherein said ignitor means includes:
    a catalytic element, and
    means operable manually from the exterior of said housing for cleaning said catalytic element.

6. The flame ionization detector in accordance with claim 1 wherein the ratio of the total volume of said air chamber, said internal passage and said exhaust chamber to the bust strength of said housing is within the safe range that, during operation of said detector, said housing can withstand an explosion therein.

7. The flame ionization detector in accordance with claim 6 wherein the lengths and inside diameters of said air inlet passage, said burner tube and said vent passage are within the range that, during operation of the detector, is capable of arresting flames resulting from an explosion in said housing.

8. The flame ionization detector in accordance with claim 1 wherein said ranges of said control means are operable to regulate the amount of excess of air in addition to the amount required for complete combination during operation of said device.

9. The flame ionization detector in accordance with claim 1, wherein said housing is made of a non-conductive ceramic which is non-corrosive in the presence of the products of combustion in said exhaust chamber.

10. The flame ionization detector in accordance with claim 9 wherein said ceramic is alumina.

* * * * *